(12) United States Patent
Lynch et al.

(10) Patent No.: US 12,245,898 B2
(45) Date of Patent: Mar. 11, 2025

(54) TEST PHANTOM FOR ULTRASOUND IMAGE QUALITY ASSESSMENT

(71) Applicant: Computerized Imaging Reference Systems, Inc., Norfolk, VA (US)

(72) Inventors: John E. Lynch, Williamsburg, VA (US); Shigeto Ono, Norfolk, VA (US)

(73) Assignee: SUN NUCLEAR CORP., Melbourne, FL (US)

( * ) Notice: Subject to any disclaimer, the term of this patent is extended or adjusted under 35 U.S.C. 154(b) by 446 days.

(21) Appl. No.: 17/363,165

(22) Filed: Jun. 30, 2021

(65) Prior Publication Data

US 2022/0008043 A1 Jan. 13, 2022

Related U.S. Application Data

(60) Provisional application No. 63/050,899, filed on Jul. 13, 2020.

(51) Int. Cl.
  *A61B 8/00* (2006.01)
  *G01S 15/89* (2006.01)
(52) U.S. Cl.
  CPC .......... *A61B 8/587* (2013.01); *G01S 15/8906* (2013.01)
(58) Field of Classification Search
  CPC ............................ A61B 8/587; G01S 15/8906
  USPC ........................................................ 73/1.86
  See application file for complete search history.

(56) References Cited

U.S. PATENT DOCUMENTS

| | | | | |
|---|---|---|---|---|
| 4,331,021 A | * | 5/1982 | Lopez | G01S 7/52052 73/1.86 |
| 4,903,523 A | * | 2/1990 | Flynn | G01H 3/005 600/437 |
| 5,312,755 A | * | 5/1994 | Madsen | G01R 33/58 324/307 |
| 5,574,212 A | * | 11/1996 | Madsen | G01S 7/5205 73/618 |
| 5,756,875 A | * | 5/1998 | Parker | G01N 29/30 367/13 |
| 6,238,343 B1 | * | 5/2001 | Madsen | G01N 29/30 600/437 |
| 6,318,146 B1 | * | 11/2001 | Madsen | A61B 8/08 324/308 |

* cited by examiner

*Primary Examiner* — Lisa M Caputo
*Assistant Examiner* — Rose M Miller
(74) *Attorney, Agent, or Firm* — Peter J. VanBergen

(57) ABSTRACT

An ultrasound test phantom includes a block of human-tissue-mimicking material having a top surface and spaced-apart groups of targets embedded therein. Each group is located at a unique depth region within the block as measured from the top surface. The targets in each group include a first linear target spaced-apart from a second linear target. For each group, the first linear target extends in a first direction at a first depth of the depth region associated therewith, and the second linear target extends in a second direction at a second depth of the depth region associated therewith. When viewed from the block's top surface, a crossing point is defined where the first direction and second direction cross at an angle between 10° and 170°. For each group, the crossing point is located along a line perpendicular to the block's top surface.

15 Claims, 4 Drawing Sheets

TEST PHANTOM FOR ULTRASOUND IMAGE QUALITY ASSESSMENT

Pursuant to 35 U.S.C. § 119, the benefit of priority from provisional application 63/050,899, with a filing date of Jul. 13, 2020, is claimed for this non-provisional application.

FIELD OF THE INVENTION

The invention relates generally to the testing of ultrasound imaging probes and systems, and more particularly to a test phantom that simplifies the alignment of an ultrasound transducer during the testing thereof.

BACKGROUND OF THE INVENTION

Periodic testing and assessment of image quality in ultrasound imaging systems utilize what is known as a "phantom". Ultrasound phantoms generally comprise a block of human-tissue-mimicking material with a set of reference targets embedded within the block. A test phantom is used to test image uniformity, distance measurement accuracy, depth of penetration, contrast resolution, spatial resolution, and dynamic range of an ultrasound imager. The human-tissue-mimicking materials replicate acoustic and physical properties of human tissue to include backscatter, speed of sound, attenuation, elastic modulus, thermal conductivity, and specific heat capacity.

Current phantoms used for ultrasound image quality testing are designed such that measurements made using a phantom require subjective evaluation by expert reviewers. While software programs exist for automated analysis, available phantoms have several limitations that reduce the utility of such software. First, distance accuracy and spatial resolution measurements made using wires embedded in a phantom will vary depending on how the ultrasound transducer is held on the phantom. The contrast resolution measurements are similarly limited by transducer orientation. For best results, contrast resolution measurements are preferably made using phantom-embedded spheres (i.e., referred to in the art as "anechoic spheres") that produce no echogenic signal under ultrasound. These spheres are embedded within an echogenic background to allow contrast-to-noise ratio measurements. Spheres of different diameters positioned at different depths within a phantom are used to perform an integrated measurement of contrast resolution within the axial, lateral and elevational imaging planes of the ultrasound imaging system. This set of spheres must be perfectly aligned with each other and with the imaging transducer. Unfortunately, due to the difficulty of aligning an ultrasound transducer with a set of embedded anechoic spheres, most ultrasound test phantoms employ anechoic cylinders. While the use of such cylinders simplifies transducer alignment, the use of cylinders as opposed to spheres only permits assessment of contrast resolution in the axial and lateral imaging planes and cannot be used to simultaneously assess contrast resolution in the elevational imaging plane.

SUMMARY OF THE INVENTION

Accordingly, it is an object of the present invention to provide an ultrasound test phantom configured to provide images that can be used in the assessment of contrast resolution, spatial resolution and distance measurement accuracy in all relevant imaging planes.

Another object of the present invention is to provide an ultrasound test phantom configured with an alignment tool to assure proper orientation of an ultrasound transducer placed on the test phantom.

Other objects and advantages of the present invention will become more obvious hereinafter in the specification and drawings.

In accordance with the present invention, an ultrasound test phantom includes a block of human-tissue-mimicking material having a planar top surface and a plurality of spaced-apart groups of targets embedded in the block. Each of the targets is adapted to appear in an ultrasonic image when exposed to ultrasonic energy. Each of the groups is located at a unique depth region within the block as measured from the block's top surface. The targets in each of the groups include a first linear target spaced-apart from a second linear target within the depth region associated therewith. For each of the groups, the first linear target extends in a first direction at a first depth of the depth region associated therewith, and the second linear target extends in a second direction at a second depth of the depth region associated therewith. When viewed from the block's top surface, a crossing point is defined wherein the first direction and second direction cross at an angle between 10° and 170°. For each of the groups, the crossing point is located along a line perpendicular to the block's top surface.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
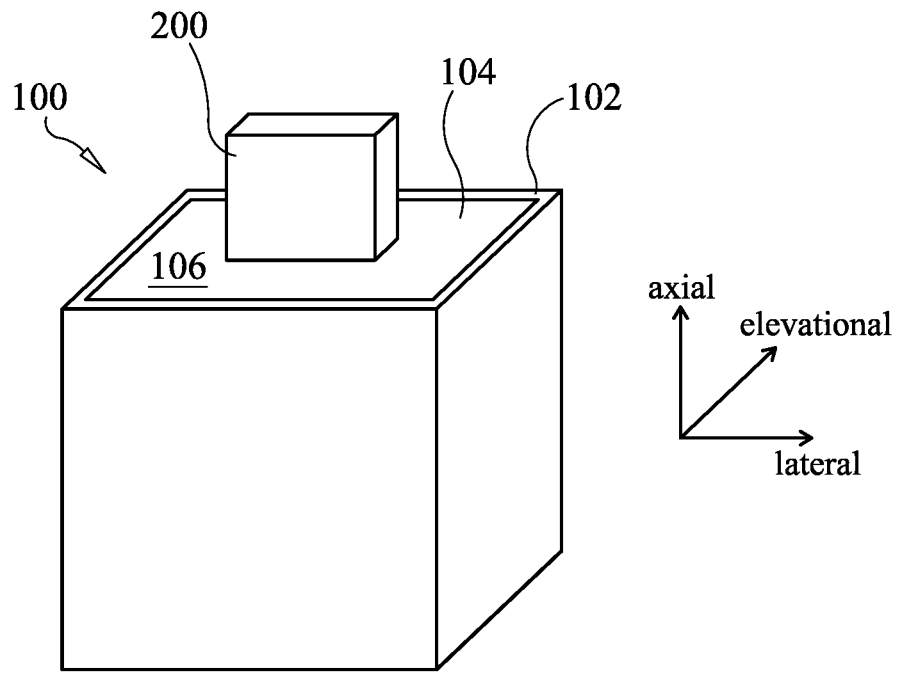
FIG. 1 is a perspective view of a conventional ultrasound test phantom with the head of an ultrasonic transducer placed thereon as it would be during testing.

Referring now to the drawings and more particularly to FIG. 1, a conventional ultrasound test phantom 100 includes an outer support container 102 filled with a three-dimensional block of gel-like human-tissue-mimicking material 104 having a top surface 106 that is planar. As is well-known in the art, a number of reference targets (not shown in FIG. 1) are embedded in material 104. The reference targets will appear as contrast elements in an ultrasound image generated by an ultrasound transducer 200.

Figure 2:
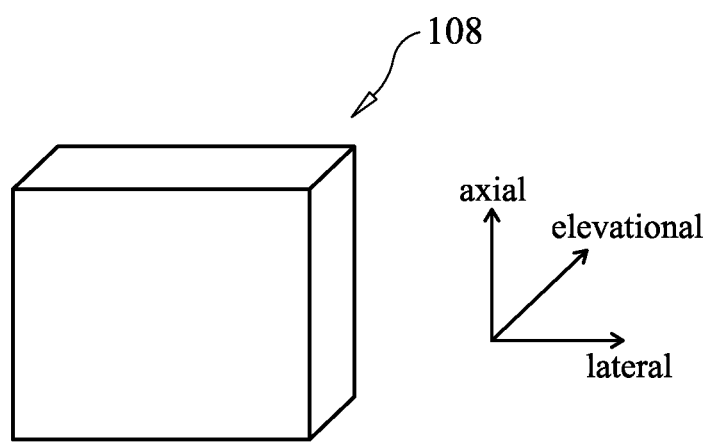
FIG. 2 is an isolated perspective of a three-dimensional beam slice of a test phantom's human-tissue-mimicking material as generated by an ultrasound transducer.

During testing, ultrasound transducer 200 is placed either directly on top surface 106, or indirectly on top surface 106 that has some protective and ultrasound-transparent media placed thereon. For example and as is known in the art, top surface 106 can have a pad (not shown) placed thereon that readily conforms to the surface of transducer 200, or top surface 106 can have a viscous liquid placed thereon. In each case, transducer 200 generates sound waves that propagate into a three-dimensional "slice" of material 104, hereinafter referred to as the "beam slice." The beam slice 108 is shown in isolation in FIG. 2 as a rectangular slice alongside the axis/plane indicators for the axial (or depth), lateral, and elevational dimensions of the beam slice. As is known in the art, ultrasound imaging systems convert the three-dimensional beam slices into a two-dimensional image slice. The image slice directly represents the axial and lateral dimensions of target objects embedded within the beam slice. The elevational dimension of a target object shows up in a two-dimensional image as a projection of the target object into the lateral dimension.

An ultrasound test phantom in accordance with the present invention will generally be constructed as just described to include material 104 with reference targets embedded therein. For purposes of the present invention, material 104 can be made of any number of materials that mimic human tissue in terms of ultrasound propagation therein such that they are compatible with medical ultrasound imaging. The preferred set of acoustic properties, as recommended by International Electrotechnical Commission (IEC) Technical Specification 62736, "Simple methods for periodic testing to verify stability of an imaging system's elementary performance," is as follows:

Speed of sound: 1540±20 m/s
Attenuation coefficient: 0.70+0.2/−0.05 dB/cm/MHz
Backscatter coefficient: $3 \times 10^{-4}$ 1/steradians*cm±10 dB at an imaging frequency of 3 MHz The above set of specifications applies to water-based hydrogels. However, hydrogels can dry out if exposed to air. As a result, many ultrasound phantoms are made of oil-based rubbers, e.g., polymers such as polyurethane, plastisol or thermoplastic elastomers. The improved durability of these rubber-based phantoms comes at the cost of image quality, as the acoustic properties do not match those listed above. However, the image quality in these phantoms is often sufficient to check the stability of image performance over time, and is therefore accepted or even preferred by many users. Accordingly, as used herein, the term "human-tissue-mimicking material" for purposes of the present invention includes hydrogels or any of the oil-based rubber materials commonly used to make phantoms provided they satisfy the following criteria:

Speed of sound in the range of 1400 to 1700 m/s
Attenuation coefficient in the range of 0.30 to 1.0 dB/cm/MHz
Backscatter coefficient in the range of $3 \times 10^{-5}$ to $3 \times 10^{-3}$ 1/steradians*cm (It is noted that while the range for backscatter coefficient is generally applicable for an imaging frequency of 3 MHz and will change for other frequencies, most standards quote the value at 3 MHz and then specify a frequency dependence of $f^4$.)

The present invention presents unique arrangements of reference targets for an ultrasound test phantom that will provide the test operator with an alignment tool to assure the proper orientation of an ultrasound transducer during the testing thereof. With proper transducer orientation, consistent and quantitative measurements of image quality can be achieved. A number of exemplary embodiments of reference target arrangements will be shown and described herein. However, it is to be understood that additional embodiments of reference target arrangements can be used and still fall within the scope of the present invention.

Figure 3:
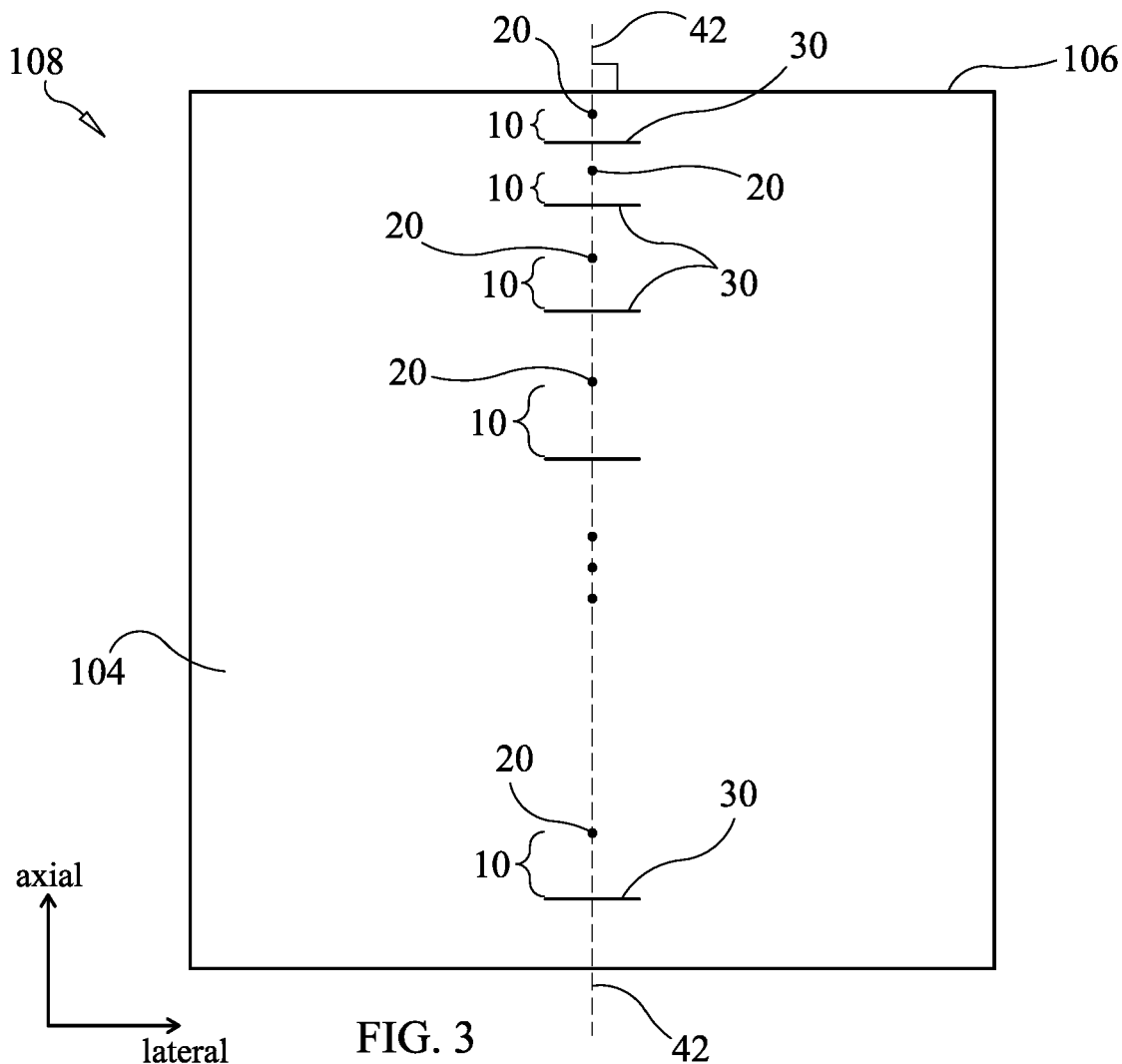
FIG. 3 is a cross-sectional view of a beam slice (such as that shown in FIG. 2) along the axial depth thereof illustrating groups of spaced-apart crossing linear targets for a test phantom in accordance with an embodiment of the present invention.
Figure 4:
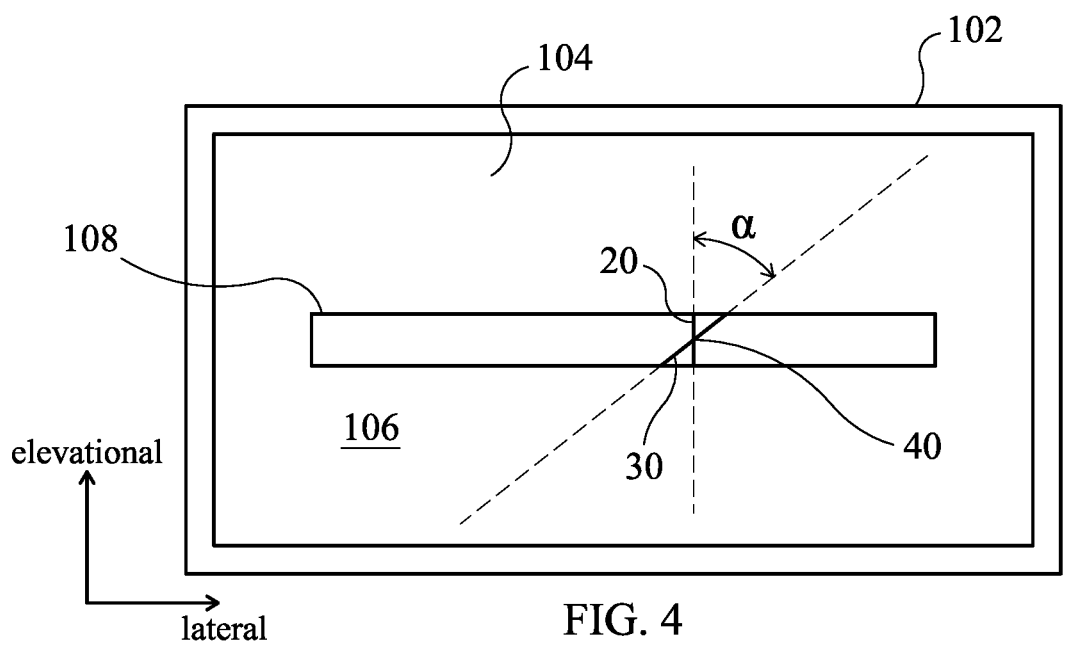
FIG. 4 is the top view of the test phantom to include to include a top view of the beam slice shown in FIG. 3 as it would be viewed by a properly oriented ultrasound transducer positioned on the top of the human-tissue-mimicking material and over the groups of crossing linear targets.

An embodiment of the alignment tool aspect of the present invention will now be explained with simultaneous reference to FIGS. 3 and 4. FIG. 3 depicts a cross-sectional view of a beam slice 108 such as that shown in FIG. 2 cut along the entire axial depth of material 104. FIG. 4 depicts the top of the present invention's test phantom with the top of a beam slice 108 projected thereon as it would be viewed by a properly oriented ultrasound transducer (not shown) positioned on top surface 106 of human-tissue-mimicking material 104 and over aligned linear targets as will be explained further below.

In general, a plurality of groups 10 of linear targets are provided with each group 10 being at a unique depth region of material 104 where each depth region is defined by the axial depth spacing between linear targets associated with a group. At a minimum, two of groups 10 are provided in material 104. However, more than two groups 10 will generally be included in a test phantom in order for the test phantom to be adaptable for use across an ultrasonic frequency spectrum that allows for testing of different types of ultrasonic transducers.

Each group 10 includes a first linear target 20 spaced apart from a second linear target 30 in the axial or depth dimension of material 104. In general, linear targets 20/30 are made from a material that will be visible in an ultrasonic image when the linear targets are exposed to ultrasonic energy. Each linear target can be a metal wire, a non-metal line, or a fabric thread without departing from the scope of the present invention. For most applications, the width (e.g., diameter) of the linear targets is smaller than the wavelength of the ultrasonic energy that it will be exposed to in material 104.

In the illustrated embodiment, each first linear target 20 extends along a first direction in the elevation dimension of the test phantom and each second linear target 30 extends along a second direction in the elevational and lateral dimensions of the test phantom such that an angle α is defined between the two directions. That is, the two directions cross one another when viewed from the perspective of top surface 106. Each group's corresponding second linear target 30 is at a different axial depth than the group's corresponding first linear target 20. In the illustrated embodiment, the crossing angle α (shown in FIG. 4) between the extension directions of linear targets 20 and 30 is approximately 45°. However, it is to be understood that both linear targets can extend in the phantom's elevational and lateral dimensions, and angle α can range from 10° to 170°. Each group's linear targets can reside in parallel planes of material 104, although this is not a requirement of the present invention. The axial depth spacing between linear targets can be same throughout the groups, or can be different without departing from the scope of the present invention. For example, in the illustrated FIG. 3 embodiment, linear targets 20/30 are spaced closer together for groups 10 near top surface 106 such that they can be useful in the alignment of a transducer whose ultrasonic energy will only penetrate to a shallow axial depth of material 104.

By virtue of their angular relationship, each group's linear targets 20/30 cross one another at a crossing point 40 when viewed from top surface 106 as illustrated in FIG. 4. For purposes of the present invention's alignment tool aspects, each group's crossing point 40 is located along a line 42 that is perpendicular to top surface 106 as illustrated in FIG. 3.

In operation, a user manipulates an ultrasound transducer being tested to align crossing points 40 in the beam slice image. Proper transducer orientation is achieved when the three-dimensional ultrasound beam slice passes through any two or more of crossing points 40 (on line 42), while a user only sees one crossing point 40 in beam slice 108 as illustrated in FIG. 4. By providing multiple groups 10 at different axial depth regions within the phantom, the present invention can be used with a variety of transducers having varied resolution depth capabilities.

Figure 5:
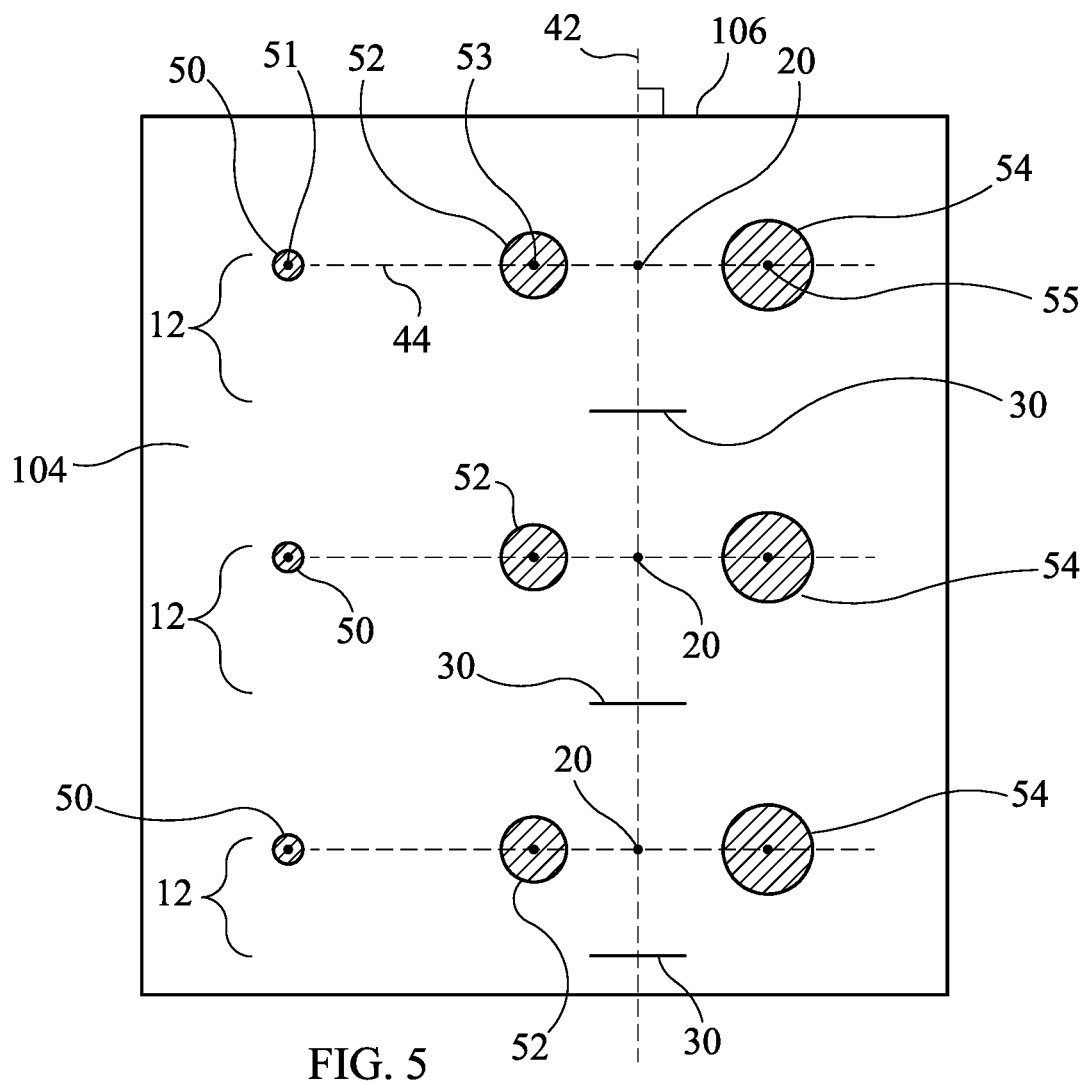
FIG. 5 is a cross-sectional view of a beam slice along the axial depth thereof illustrating groups of spaced-apart crossing linear targets and anechoic spheres for a test phantom in accordance with another embodiment of the present invention.
Figure 6:
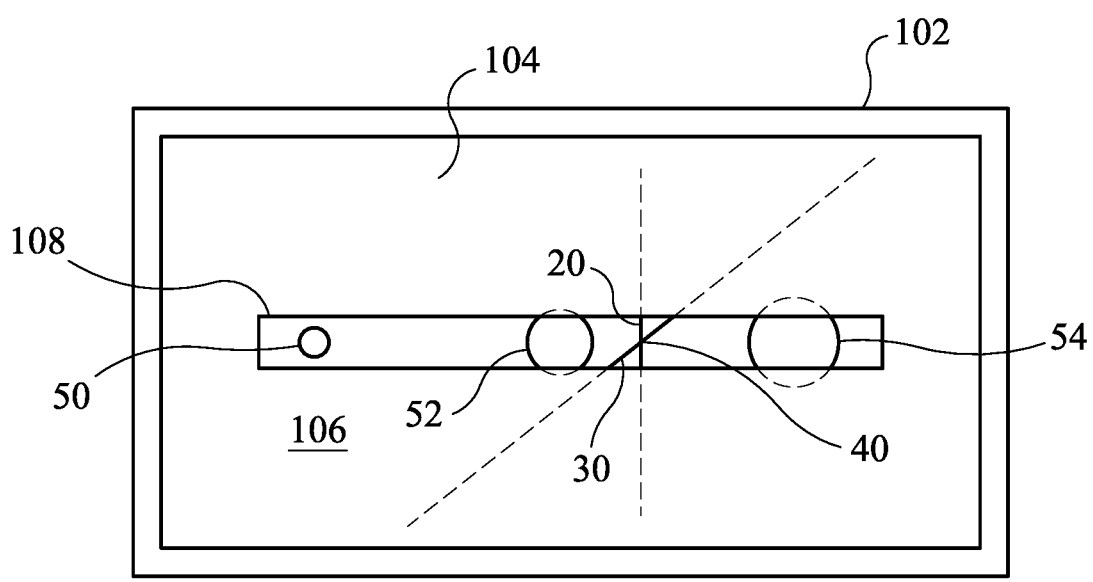
FIG. 6 is the top view of the test phantom to include a top view of the beam slice shown in FIG. 5 as it would be viewed by a properly oriented ultrasound transducer positioned on the top of the human-tissue-mimicking material and over the groups of crossing linear targets and anechoic spheres.

Phantoms in accordance with the present invention can also include anechoic spheres for contrast resolution measurements. As is known in the art of ultrasound phantoms, an anechoic sphere is made of human-tissue-mimicking material that lacks the inclusion of echogenic contrast agents. One such phantom will now be explained with simultaneous reference FIGS. 5 and 6. FIG. 5 depicts a cross-sectional view of a beam slice such as that shown in FIG. 2 cut along the entire axial depth of material 104. FIG. 6 depicts the top of the test phantom with the top of a beam slice 108 projected thereon as it would be viewed by a properly oriented ultrasound transducer (not shown) positioned on top surface 106 of human-tissue-mimicking material 104 and over aligned anechoic spheres and the above-described linear targets.

Similar to the previously-described embodiment, a plurality of groups 12 of targets are provided with each group 12 being at a unique depth region of material 104. Each such group includes the above-described linear targets 20/30, and one or more of groups 12 further includes one or more (e.g., three in the illustrated embodiment) anechoic spheres. The centers of the anechoic spheres associated with each group 12 are aligned with one another and with the group's linear target 20. In the illustrated embodiment, three anechoic spheres 50/52/54 of differing diameter are included in each group 12. For each group 12, the respective centers 51/53/55 of spheres 50/52/54 and corresponding linear target 20 are aligned with one another at a common axial depth as indicated by dashed line 44.

In operation, a user manipulates an ultrasound transducer being tested to align crossing points 40 in the beam slice image as previously described. Proper transducer orientation is achieved when the three-dimensional ultrasound beam slice passes through any two or more of crossing points 40 (on line 42), while a user only sees one crossing point 40 in beam slice 108 as illustrated in FIG. 6. At the same time, a user will also be able to see one or more of spheres 50/52/54 depending on the wavelength of the transducer being tested. By providing multiple groups 12 of spheres/linear targets at different axial depth regions within the phantom, the present invention can be used with a variety of transducers having varied resolution depth capabilities.

The advantages of the present invention are numerous. By orienting a group of anechoic targets in the same imaging plane as corresponding group(s) of linear targets, consistent acquisition of anechoic targets for use in contrast resolution measurements can be ensured. The linear targets are designed to have further utility for measuring spatial resolution. The height of the linear targets (i.e., in the axial or depth dimension of the phantom) can be used to directly assess axial resolution, while the lateral and elevational resolution can be determined mathematically using the width of each linear target in a crossing pair and the crossing angle between a group's linear target extension directions. The linear targets can also be used for distance measurement accuracy tests. The angular relationship between the linear targets provides for measurements in the elevational plane which is important for three-dimensional imaging probes.

Although the invention has been described relative to specific embodiments thereof, there are numerous variations and modifications that will be readily apparent to those skilled in the art in light of the above teachings. For example and as mentioned above, an ultrasound test phantom in accordance with the present invention can include a soft material layer on the top surface of the phantom that conforms to the shape of the ultrasound transducer under test. A conformal coupling pad facilitates performance of image uniformity tests on all types of transducers, while also ensuring that the entire field of view of the transducer is tested when performing other tests. A conformal coupling pad eliminates the need for a water bath or curved transducer surface to achieve full coupling of all transducer elements in a curved transducer to the phantom surface. Full coupling is essential for accurate assessment of image uniformity and is helpful in standardizing the image acquisition process by minimizing the role of probe coupling as a source of variation when assessing image quality.

In other embodiments of the present invention, the above-described anechoic spheres can be replaced by cylinders. Cylinders are easier to embed within a phantom and measurements made using them are less sensitive to probe orientation errors. However, contrast resolution measurements made on cylinders do not assess the full three-dimensional performance of the ultrasound system.

Figure 7:
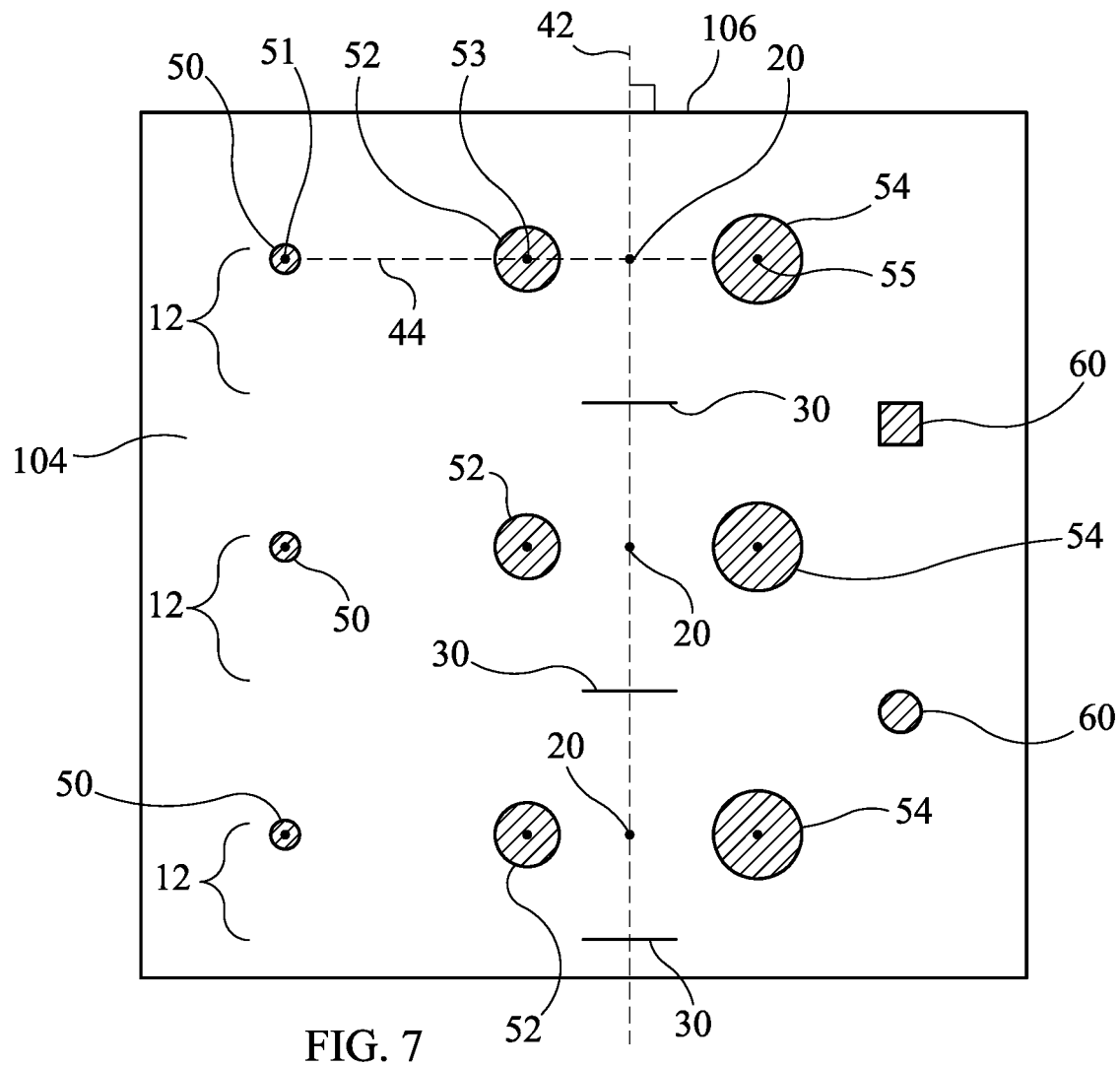
FIG. 7 is a cross-sectional view of a beam slice along the axial depth thereof illustrating groups of spaced-apart crossing linear targets, anechoic spheres, and greyscale targets for a test phantom in accordance with another embodiment of the present invention.

In still other embodiments of the present invention and as illustrated in FIG. 7, greyscale targets 60 (e.g., made using cylindrical or spherical targets) with varying levels of echogenicity can be additionally embedded in material 104. Such greyscale targets are of secondary importance relative to the above-described anechoic targets when assessing image quality such that they do not need to be grouped with the primary set of targets that includes the crossing linear targets and, in some embodiments, the anechoic targets.

Some embodiments of the present invention can utilize a general-purpose phantom design to cover a wide variety of transducer shapes and imaging frequencies used in clinical medical ultrasound systems. However, the present invention is not so limited as other embodiments of the present invention could utilize specialized phantom designs optimized for unusual transducer shapes and sizes.

Ultrasound test phantoms in accordance with the present invention can be used in conjunction with a software analysis package to automate the measurement of image quality test parameters. The software would be designed to automatically separate out the image field-of-view from non-imaging background features, and recognize the coordinate system used in the image data (i.e., curvilinear versus linear). Further, the layout of imaging targets in the phantom can be designed to minimize the number images needed to completely assess image quality.

It is therefore to be understood that, within the scope of the appended claims, the invention may be practiced other than as specifically described.

What is claimed as new and desired to be secured by Letters Patent of the United States is:

1. An ultrasound test phantom, comprising:
   a block of human-tissue-mimicking material, said block having a planar top surface; and
   a plurality of spaced-apart groups of targets embedded in said block wherein each of said targets is adapted to appear in an ultrasonic image when exposed to ultrasonic energy, each of said groups located at a unique depth region within said block as measured from said top surface, said targets in each of said groups including a first linear target spaced-apart from a second linear target within said depth region associated therewith,
   wherein, for each of said groups, said first linear target extends in a first direction at a first depth of said depth region associated therewith, and said second linear target extends in a second direction at a second depth of said depth region associated therewith,
   wherein, when viewed from said top surface, a crossing point is defined wherein said first direction and said second direction cross at an angle between 10° and 170°, and
   wherein, for each of said groups, said crossing point is located along a line perpendicular to said top surface.

2. An ultrasound test phantom as in claim 1 wherein, for each of said groups, said first direction and said second direction lie in parallel planes of said depth region associated therewith.

3. An ultrasound test phantom as in claim 1, wherein each said first linear target and each said second linear target are selected from the group consisting of metal wires, non-metal lines, and fabric threads.

4. An ultrasound test phantom as in claim 1, wherein said targets in at least one of said groups further includes at least one anechoic sphere having a center at said first depth.

5. An ultrasound test phantom as in claim 1, wherein said targets in at least one of said groups further includes a plurality of different-diameter and spaced-apart anechoic spheres, each of said anechoic spheres having a center at said first depth.

6. An ultrasound test phantom as in claim 1, wherein spacing between said first linear target and said second linear target is identical for at least a portion of said groups.

7. An ultrasound test phantom, comprising:
   a block of material having a planar top surface, said material selected from the group consisting of hydrogels and oil-based rubbers having human-tissue-mimicking properties, said block adapted to have ultrasonic energy transmitted therein at said top surface; and
   a plurality of spaced-apart groups of targets embedded in said block wherein each of said targets in at least two of said groups is adapted to appear in an ultrasonic image when exposed to the ultrasonic energy, each of said groups located at a unique depth region within said block as measured from said top surface, said targets in each of said groups including a first linear target spaced-apart from a second linear target within said depth region associated therewith,
   wherein, for each of said groups, said first linear target extends in a first direction at a first depth of said depth region associated therewith, and said second linear target extends in a second direction at a second depth of said depth region associated therewith,
   wherein, when viewed from said top surface, a crossing point is defined wherein said first direction and said second direction cross at an angle between 10° and 170°, and
   wherein, for each of said groups, said crossing point is located along a line perpendicular to said top surface.

8. An ultrasound test phantom as in claim 7 wherein, for each of said groups, said first direction and said second direction lie in parallel planes of said depth region associated therewith.

9. An ultrasound test phantom as in claim 7, wherein each said first linear target and each said second linear target are selected from the group consisting of metal wires, non-metal lines, and fabric threads.

10. An ultrasound test phantom as in claim 7, wherein said targets in at least one of said groups further includes at least one anechoic sphere having a center at said first depth.

11. An ultrasound test phantom as in claim 7, wherein said targets in at least one of said groups further includes a plurality of different-diameter and spaced-apart anechoic spheres, each of said anechoic spheres having a center at said first depth.

12. An ultrasound test phantom as in claim 7, wherein spacing between said first linear target and said second linear target is identical for at least a portion of said groups.

13. An ultrasound test phantom, comprising:
   a block of human-tissue-mimicking material, said block having a planar top surface;
   a plurality of spaced-apart groups of targets embedded in said block wherein each of said targets is adapted to appear in an ultrasonic image when exposed to ultrasonic energy, each of said groups located at a unique depth region within said block as measured from said top surface;
   said targets in each of said groups including a first linear target spaced-apart from a second linear target within said depth region associated therewith; and
   said targets in at least one of said groups further including a plurality of different-diameter and spaced-apart anechoic spheres, wherein each of said anechoic spheres has a center at said first depth associated with a corresponding said at least one of said groups,
   wherein, for each of said groups, said first linear target extends in a first direction at a first depth of said depth region associated therewith, and said second linear target extends in a second direction at a second depth of said depth region associated therewith,
   wherein spacing between said first linear target and said second linear target is identical for at least a portion of said groups,
   wherein, when viewed from said top surface, a crossing point is defined wherein said first direction and said second direction cross at an angle between 10° and 170°, and
   wherein, for each of said groups, said crossing point is located along a line perpendicular to said top surface.

14. An ultrasound test phantom as in claim 13 wherein, for each of said groups, said first direction and said second direction lie in parallel planes of said depth region associated therewith.

15. An ultrasound test phantom as in claim 13, wherein each said first linear target and each said second linear target are selected from the group consisting of metal wires, non-metal lines, and fabric threads.

* * * * *